United States Patent
Kim et al.

(10) Patent No.: US 8,822,714 B2
(45) Date of Patent: Sep. 2, 2014

(54) MORE ADVANCED PREPARATION METHOD OF ORGANIC-TRANSITION METAL HYDRIDE COMPLEXES CONTAINING ARYL GROUP OR ALKYL GROUP AS HYDROGEN STORAGE MATERIALS

(71) Applicants: Jong Sik Kim, Daejeon (KR); Dong Ok Kim, Seoul (KR); Hee Bock Yoon, Daejeon (KR); Jaesung Park, Daejeon (KR); Hyo Jin Jeon, Incheon (KR); Gui Ryong Ahn, Daejeon (KR); Dong Wook Kim, Daejeon (KR); Jisoon Ihm, Seoul (KR); Moon-Hyun Cha, Seoul (KR)

(72) Inventors: Jong Sik Kim, Daejeon (KR); Dong Ok Kim, Seoul (KR); Hee Bock Yoon, Daejeon (KR); Jaesung Park, Daejeon (KR); Hyo Jin Jeon, Incheon (KR); Gui Ryong Ahn, Daejeon (KR); Dong Wook Kim, Daejeon (KR); Jisoon Ihm, Seoul (KR); Moon-Hyun Cha, Seoul (KR)

(73) Assignee: Hanwha Chemical Corporation, Seoul (KR)

( * ) Notice: Subject to any disclaimer, the term of this patent is extended or adjusted under 35 U.S.C. 154(b) by 60 days.

(21) Appl. No.: 13/723,883

(22) Filed: Dec. 21, 2012

(65) Prior Publication Data
US 2013/0123527 A1    May 16, 2013

Related U.S. Application Data

(62) Division of application No. 12/538,209, filed on Aug. 10, 2009, now Pat. No. 8,354,553.

(30) Foreign Application Priority Data
Aug. 11, 2008  (KR) .................. 10-2008-0078334

(51) Int. Cl.
*C07F 7/28* (2006.01)
*C07F 1/00* (2006.01)

(52) U.S. Cl.
CPC ... C07F 7/28 (2013.01); C07F 1/00 (2013.01); *C07F 1/005* (2013.01)
USPC ............. 556/52; 556/58; 556/87; 556/112; 556/121; 556/140; 502/102

(58) Field of Classification Search
None
See application file for complete search history.

(56) References Cited

U.S. PATENT DOCUMENTS

| | | | | |
|---|---|---|---|---|
| 3,617,218 | A * | 11/1971 | Van Tamelen et al. | ....... 423/646 |
| 4,957,727 | A | 9/1990 | Bogdanovic | |
| 6,410,657 | B1 * | 6/2002 | Ko et al. | ....... 525/338 |
| 7,790,911 | B2 | 9/2010 | Kim et al. | |
| 2010/0022791 | A1 | 1/2010 | Ihm et al. | |

FOREIGN PATENT DOCUMENTS

| | | |
|---|---|---|
| EP | 2 098 530 | 9/2009 |
| KR | 10-2008-0024975 | 3/2008 |
| KR | 10-2008-0024976 | 3/2008 |
| WO | 2008/032985 | 3/2008 |

OTHER PUBLICATIONS

J. Am. Chem. Soc. 1955, 77, 5838-5840.*
J. Am. Chem. Soc. 1966, 88, 1138-1140.*
J. Chem. Soc. Chem. Commun. 1972, 481-482.*
J. Dobado et al., "Multiple Bonding in Four-Coordinated Titanium(IV) Compounds", Inorg. Chem., 2000, 39, 2831-2836.
Bogdanovic, B. et al., "Catalytic synthesis . . . mild conditions", Angew. Chem.. Int. Ed. Engl. (1980) 10: 819-9.
T. Chu et al, "Reducing Action of Sodium Naphthalide inTetrahydrofuran Solution. I. The Reduction of Cobalt (II) Chloride[1]", J. Am. Chem. Soc., vol. 77, Nov. 20, 1955, p. 5838-5840.

* cited by examiner

*Primary Examiner* — Fereydoun G Sajjadi
*Assistant Examiner* — Medhanit Bahta
(74) *Attorney, Agent, or Firm* — Clark & Brody

(57) ABSTRACT

The present invention relates to a more advanced preparation method of organic-transition metal hydride as a hydrogen storage material, precisely a more advanced preparation method of organic-transition metal hydride containing aryl or alkyl group that facilitates safe and reverse storage of massive amount of hydrogen. The present invention relates to a preparation method of an organic-transition metal hydride comprising the steps of preparing a complex reducing agent composition by reacting alkali metal, alkali earth metal or a mixture thereof and (C10-C20) aromatic compound in aprotic polar solvent and preparing organic-transition metal hydride by reacting the prepared complex reducing agent composition and organic transition metal halide. The method of the present invention has advantages of minimizing the numbers and the amounts of byproducts by using a complex reducing agent and producing organic-transition metal hydride safely without denaturation under more moderate reaction conditions.

6 Claims, No Drawings

MORE ADVANCED PREPARATION METHOD OF ORGANIC-TRANSITION METAL HYDRIDE COMPLEXES CONTAINING ARYL GROUP OR ALKYL GROUP AS HYDROGEN STORAGE MATERIALS

This application is a Divisional of U.S. Ser. No. 12/538,209 filed on Aug. 10, 2009, which claims priority of Korean application no 10-2008-0078334 filed on Aug. 11, 2008.

TECHNICAL FIELD

The present invention relates to a preparation method of organic-transition metal hydride as a hydrogen storage material, wherein the organic-transition metal hydride absorbs hydrogen to store it.

BACKGROUND ART

Many research groups proposed different hydrogen storage materials such as metal hydrides, chemical hydrides ($NaBH_4$, $KBH_4$, $LiBH_4$, etc), metal-organic framework (MOF), nano-structure materials (CNT, GNF, etc), polymer-metal complex compounds, etc. However, these proposed hydrogen storage materials have disadvantages for commercialization as storage materials, for example; 1) poor hydrogen storage capacity that cannot even reach the minimum hydrogen storage rate (6 wt. %) proposed by US DOE (department of energy) for practical use; 2) poor reproducibility of hydrogen storage capacity; 3) requiring tough conditions for hydrogen absorption and desorption; 4) structural disintegration during hydrogen absorption and desorption; and 5) requiring the development of reproduction process.

In the case of the organic-transition metal hydride recently developed and applied for patent by Hanwha Chemical Cooperation R&D Center, it seems to be adequate for commercialization owing to the advanced properties such as 1) improved hydrogen storage capacity with high efficiency, compared with the conventional hydrogen storage material because of Kubas binding between hydrogen and a specific transition metal (Ti, Sc, V, etc); 2) moderate conditions for hydrogen absorption and desorption (absorption: 25° C., 30 atmospheric pressure; desorption: 100° C., 2 atmospheric pressure); and 3) no-structural disintegration during hydrogen absorption and desorption (Korean Patent Application Numbers 10-2007-0090753, 10-2007-0090755, and 10-2008-0020467).

Korean Patent Application No 10-2007-0090753 and Korean Patent Application No 10-2007-0020467 describe methods for preparing organic-transition metal hydride based on hydrodehalogenation (-M-X bond→-M-H bond) using a hydrogen source and a catalyst. However, these methods cannot avoid the problem caused by catalytic poisoning and side-reaction by inorganic hydroxide used as a neutralizing agent. Besides, separation and purification of a produce is not easy and various byproducts are produced by solvent.

To overcome the said problems, Korean Patent Application No 10-2008-0020467 provides a method to produce organic-transition metal aluminum hydride complex by reacting organic transition metal halide and aluminum hydride compound and then to produce organic-transition metal hydride by reacting the produced organic-transition metal-aluminum hydride complex with Lewis base.

However, the Korean Patent Application No 10-2008-0020467 has the following problems.

First, in relation to the reaction step, a target product is produced by 2-step reaction. Thus, this reaction exhibits lower efficiency and takes longer time, compared with 1-step reaction.

Second, in relation to the process of separation and purification of the intermediate (organic-transition metal-aluminum hydride complex) produced from the first reaction step, alcohols used for separation and purification of the intermediate are reacted with the intermediate to produce diverse byproducts.

Third, in relation to the separation and purification of the final product produced from the second reaction step, triethyl amine and butyl lithium used as Lewis base are very well dissolved in a polar or non-polar solvent, so that it is very difficult to separate these compounds from the product completely when they are present as non-reactants.

Therefore, the Korean Patent Application No 10-2008-0020467 is limited in production of organic-transition metal hydride with high yield because of the said problems.

DISCLOSURE

Technical Problem

It is an object of the present invention to provide a preparation method of organic-transition metal hydride which facilitates hydrogen storage with high capacity. high efficiency but overcomes the difficulties in separation and purification of a product.

It is also an object of the present invention to provide a preparation method of organic-transition metal hydride that can be used as a hydrogen storage material for operating small to medium size fuel cells because of comparatively moderate conditions required for hydrogen absorption and desorption, compared with the conventional hydrogen storage materials.

Technical Solution

To overcome the said problems, the present invention provides a preparation method of organic-transition metal hydride in which a complex reducing agent having strong reducing power is used for reaction and the numbers and the amounts of byproducts are minimized under comparatively moderate reaction conditions.

More precisely, the method of the present invention comprises the following steps:

a) preparing a complex reducing agent composition by reacting alkali metal, alkali earth metal or a mixture thereof with(C10-C20) aromatic compound in aprotic polar solvent; and b) preparing organic-transition metal hydride by reacting the prepared complex reducing agent composition and organic-transition metal halide.

In step a), the alkali metal, alkali earth metal or the mixture thereof provides electrons in the presence of aprotic polar solvent and the aromatic ring compound receives the electrons, resulting in the preparation of an activated complex reducing agent composition.

In step b), the activated complex reducing agent composition induces dehalogenation of the organic-transition metal halide and the aprotic polar solvent provides hydrogen, resulting in the preparation of organic-transition metal hydride.

In step b), the reaction temperature is −80-50° C., preferably −50-30° C., and more preferably −30-25° C. If the reaction temperature is lower than −80° C., the reaction cannot be finished. If the reaction temperature is higher than 50° C., the produced organic-transition metal hydride might be decomposed.

In step b), the reaction time is 1-72 hours, preferably 1-48 hours, and more preferably 1-24 hours. If the reaction time is less than one hour, the reaction cannot be finished, and if the reaction time is longer than 72 hours, the produced organic-transition metal hydride might be decomposed.

After step b), the produced organic-transition metal hydride can be separated by using one or more non-polar solvents selected from the group consisting of pentane, toluene, benzene, ether and their derivatives.

The non-polar solvent can be one or more compounds selected from the group consisting of pentane, toluene, benzene and their derivatives. When a polar solvent containing alcohol is used, there might be side reaction of organic-transition metal hydride and the organic-transition metal hydride and the byproduct are dissolved in the solvent, which makes the separation and purification of organic-transition metal hydride difficult.

The alkali metal or alkali earth metal is strong electron-donor metal, which is exemplified by Li, Na, K, Rd, Cs, Fr, Mg, Ca, Sr, Ba and Rd. Among these, alkali metal having stronger reducing power is preferred and Li in the form of small granules is more preferred.

In the present invention, the aromatic ring compound is the electron recipient and contains at least two benzene rings or fused with two benzene rings, which can be selected from the group consisting of naphthalene, biphenyl, phenanthrene, anthracene, trans-stilbene and their derivatives. But, naphthalene and its derivatives are more preferred because they are easy to handle and have excellent sublimation property and are easy to eliminate after the reaction.

The molar ratio (A:B) of transition metal (A) of organic-transition metal halide to alkali metal or alkali earth metal or a mixture thereof and aromatic ring compound (B) is preferably 1:0.0001-1:10. In this range, production of byproducts can be reduced.

The aprotic polar solvent is the source of hydrogen and at the same time acts as a solvent, which can be selected from the group consisting of tetrahydrofuran (THF), 1,2-dimethoxyethane (DME), dioxane (DXN), diethylene glycol dimethyl ether (Diglyme), dimethyl formamide (DMF), dimethylsulfoxide (DMSO), dimethylacetamide (DMA), hexamethyl phosphoramide (HMPA) and their derivatives. Preferably, the aprotic polar solvent can be selected from the group consisting of tetrahydrofuran (THF), 1,2-dimethoxyethane (DME), dioxane (DXN), diethylene glycol dimethyl ether (Diglyme), dimethyl formamide (DMF) and their derivatives. It is more preferred to select one or more compounds among tetrahydrofuran (THF), 1,2-dimethoxyethane (DME) and their derivatives because they have lower boiling points favoring the application of Schlenk technology.

In this invention, reaction of each step is preferably performed based on Schlenk technology under one or more gases selected from the group consisting of Ar, N and He and in a glove box considering instability of the product.

In this invention, the organic-transition metal hydride is represented by formula 1 and the organic-transition metal halide is represented by formula 2.

  Formula 1

  Formula 2

In formula 1, $B^1$ is straight or branched (C2-C20) alkyl, (C6-C20) aryl, (C3-C20) hetero aryl or (C6-C20) ar (C2-C20) alkyl, and the alkyl can contain unsaturated bond in its carbon chain. Carbon atom composing aryl or aralkyl in $B^1$ can be substituted with hetero atom selected from the group consisting of N, $O_2$, and S.

$B^1$ can be replaced with one or more substituents selected from the group consisting of —$NO_2$, —NO, —$NH_2$, —$R^1$, —$OR^2$, —$(CO)R^3$, —$SO_2NH_2$, $SO_2X^1$, —$SO_2Na$, —$(CH_2)_k$SH and —CN, and in that case, $R^1$-$R^3$ of the substituent can be selected from the group consisting of straight or branched (C1-C30) alkyls or (C6-C20) aryls, respectively.

A herein is O or S, $X^1$ is a halogen element, and k is an integer of 0-10. $M^1$ is one or more elements selected from the group consisting of transition metal elements having the valence of at least 2, more precisely, one or more elements selected from the group consisting of Ti, V and Sc. m is an integer that a valence of $M^1$ −1, more precisely an integer of 1-6 and more preferably an integer of 2-4. n is an integer of 1-10 and more preferably an integer of 2-6.

In formula 2, X is a halogen element selected from the group consisting of F, Cl, Br and I.

More precisely, $B^1$ of formula 1 can be selected among those compounds represented by the following structures.

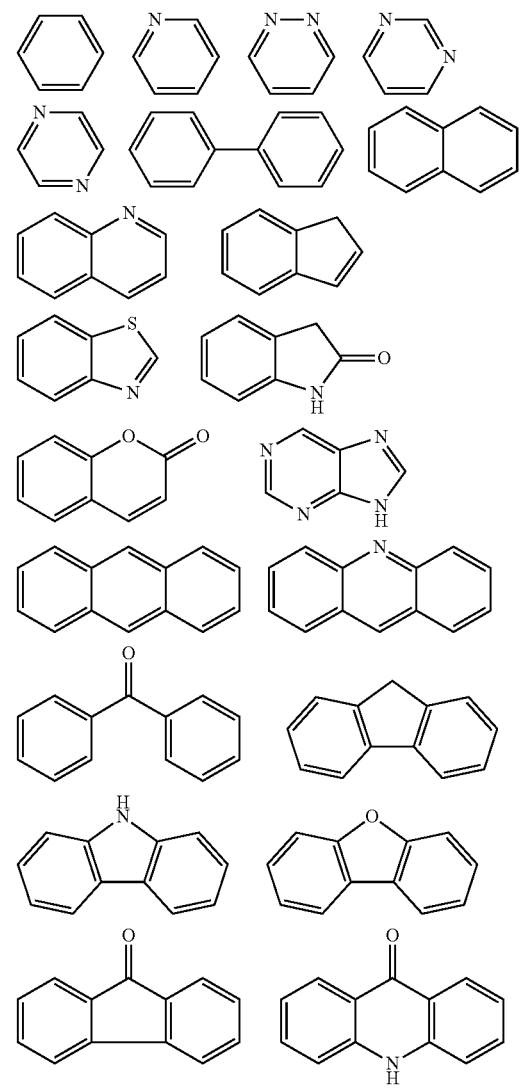

The present invention also provides a preparation method of organic-transition metal hydride, in which the organic-transition metal hydride is selected from those compounds represented by the following formula 3 and the organic-transition metal halide is selected from those compounds represented by the following formula 4.

$$B^2\text{-}(M^2H_a)_b \qquad \text{Formula 3}$$

$$B^2\text{-}(M^2X_a)_b \qquad \text{Formula 4}$$

In formula 3 and formula 4, $B^2$ is selected from the group consisting of fused ring compounds containing cyclopentadiene derivatives or cyclopentadiene. $B^2$ can be replaced with one or more substituents selected from the group consisting of —$NO_2$, —NO, —$NH_2$, —$R^1$, —$OR^2$, —(CO)R3, —$SO_2NH_2$, $SO_2X^1$, —$SO_2Na$, —$(CH_2)_k SH$ and —CN, and in that case, $R^1$-$R^3$ of the substituent can be selected from the group consisting of straight or branched (C1-C30) alkyls or (C6-C20) aryls, respectively.

$X^1$ is a halogen element, and k is an integer of 0-10. $M^2$ is one or more elements selected from the group consisting of transition metal elements having the valence of at least 2, more precisely, one or more elements selected from the group consisting of Ti, V and Sc. a is an integer that a valence of $M^2$−1, precisely an integer of 1-6 and more preferably an integer of 2-4. b is limited to the number of rings of the fused ring compound containing cyclopentadiene derivatives or cyclopentadiene, which is an integer of 1~10 and more preferably an integer of 2-6.

In $B^2$, the fused ring compound containing cyclopentadiene derivatives or cyclopentadiene is selected from the group consisting of cyclopentadienyl, methylcyclopentadienyl, dimethylcyclopentadienyl, tetramethylcyclopentadienyl, pentamethylcyclopentadienyl, butylcyclopentadienyl, sec-butylcyclopentadienyl, tert-butylmethylcyclopentadienyl, trimethylsilylcyclopentadienyl, indenyl, methylindenyl, dimethylindenyl, ethylindenyl, isopropylindenyl, fluorenyl, methylfluorenyl, dimethylfluorenyl, ethylfluorenyl and isopropylfluorenyl.

Advantageous Effect

The preparation method of the present invention uses a complex reducing agent having strong reducing power, so that it can overcome the problems of separation and purification of organic-transition metal hydride and gives the product stably with high yield without denaturation.

The preparation method of the present invention can minimize the numbers and the amounts of various byproducts produced from the reaction. And the organic-transition metal hydride produced by the method can be used as a hydrogen storage material for operating small to medium size fuel cells because of comparatively moderate conditions required for hydrogen absorption and desorption, compared with the conventional hydrogen storage materials.

BEST MODE

Hereinafter, the preparation method of organic-transition metal hydride is described in detail with examples. In these examples, phenoxytitanium trichloride and cyclopentadienyltitanium trichloride were selected as the reactant organic-transition metal halide because 1) they are easy to handle at room temperature; 2) when they are used, the product organic-transition metal hydride has a low molecular weight but has comparatively large hydrogen storage capacity; and 3) they are easily separated and purified owing to high solubility in non-polar solvent.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Preparation of Phenoxytitanium Trihydride

<1-1>Preparation of 1,2-Dimethoxyethane (DME) Complex Reducing Agent

A complex reducing agent was prepared by reacting lithium (0.034 g/4.86 mmol) and naphthalene (0.622/4.86 mmol) in 70 ml of 1,2-dimethoxyethane under Ar flow in a 250 ml 1-neck round flask for 10 hours.

<1-2>Preparation of Phenoxytitanium Trihydride

Phenoxytitanium trichloride (0.4 g/1.62 mmol) was dissolved in 30 ml of 1,2-dimethoxyethane(DME) under Ar flow in a 100 ml 2-neck round flask (reactant 1).

The prepared lithium/naphthalene/1,2-dimethoxyethane (DME) complex reducing agent was slowly dropped in the reactant 1, followed by reflux at 10° C. for 18 hours and then the reaction was terminated.

The reaction solvent 1,2-dimethoxyethane was eliminated by Schlenk method under Ar and then the reaction product phenoxytitanium trihydride was separated.

The solvent was eliminated by Schlenk method to give phenoxytitanium trihydride with the yield of 99%.

Yield: 99% $^1$H-NMR (CD$_3$CN-d$_3$) γ(ppm): 7.28(d, 1H), 6.95(t, 2H), 6.85(t, 2H), 7.62 (s, 3H) ESI-MS (positive mode), m/z(relative intensity): [C$_6$H$_5$—O—Ti—H$_3$]+144(9.9), 145 (9.4), 146(100), 147(23), 148(10.1) Anal. Calc. for C$_6$H$_5$OTiH$_3$: C, 50.0; H, 5.6. Found: C, 49.5; H, 5.4%.

To identify byproducts and products generated in Example 1, $^{35}$Cl-NMR, XRD, IC, EDX, ESR, and XRF were performed. From the results of XRD and $^{35}$Cl-NMR, it was confirmed that LiCl was produced as a byproduct. Separation and purification was performed by using benzene. As a result, a small amount of LiCl or non reactant was included in the product, even though the amount was too small to be detected by XRD and $^{35}$Cl-NMR.

To confirm whether LiCl and non reactant were actually included in the reaction product, IC and EDX were performed. As a result, it was confirmed that LiCl was included approximately 0.5% in the product.

From the separation and purification test, it was confirmed that LiCl was hardly detected in the product. And benzene was preferred as the solvent for separation and purification. ESR analysis was also performed with the product. As a result, oxidation number of Ti was +4. From the result of XRF assay, it was confirmed that the weight content of Ti was 33.2 wt % (theoretical value=33.27 wt %), indicating that high purity product was obtained.

EXAMPLE 2

Preparation of Cyclopentadienyltitanium Trihydride

<2-1>Preparation of Sodium/Naphthalene/Tetrahydrofuran (Thf) Complex Reducing Agent A complex reducing agent was prepared by reacting sodium (0.034 g/4.86 mmol) and naphthalene (0.622/4.86 mmol) in 70 ml of tetrahydrofuran under Ar flow in a 250 ml 1-neck round flask for 10 hours.

<2-2>Preparation of Cyclopentadienyltitanium Trihydride cyclopentadienyltitanium trichloride (0.355 g/1.62 mmol) was dissolved in 30 ml of tetrahydrofuran (THF) under Ar flow in a 100 ml 2-neck round flask (reactant 1).

The prepared sodium/naphthalene/tetrahydrofuran (THF) complex reducing agent was slowly dropped in the reactant 1, followed by reflux at 10° C. for 18 hours and then the reaction was terminated.

The reaction solvent tetrahydrofuran was eliminated by Schlenk method under Ar and then the reaction product cyclopentadienyltitanium trihydride was separated by using toluene.

The solvent was eliminated by Schlenk method to give cyclopentadienyltitanium trihydride with the yield of 98%.

Yield: 98% $^1$H-NMR (benzene-d$_6$) γ(ppm): 5.995(t, 5H), 10.62 (s, 3H) ESI-MS (positive mode), m/z(relative intensity): [C$_5$H$_5$—Ti—H$_3$]+114(9.9), 115(9.4), 116(100), 117(23), 118(10.1) Anal. Calc. for C$_5$H$_5$TiH$_3$: C, 51.8; H, 6.9. Found: C, 50.5; H, 6.1%.

To identify byproducts and products generated in Example 2, $^{35}$Cl-NMR, XRD, IC, EDX, ESR, and XRF were performed and the results are as follows. From the results of XRD and $^{35}$Cl-NMR, it was confirmed that NaCl was produced as a byproduct. Separation and purification was performed by using toluene. As a result, a small amount of NaCl or non reactant was included in the product, even though the amount was too small to be detected by XRD and $^{35}$Cl-NMR.

To confirm whether NaCl and non reactant were actually included in the reaction product, IC and EDX were performed. As a result, it was confirmed that NaCl was included approximately 0.9% in the product.

From the separation and purification test, it was confirmed that NaCl was hardly detected in the product. And toluene was preferred as the solvent for separation and purification.

ESR analysis was also performed with the product. As a result, oxidation number of Ti was +4. From the result of XRF assay, it was confirmed that the weight content of Ti was 40.3 wt % (theoretical value=41.3 wt %), indicating that high purity product was obtained.

The present application contains subject matter related to Korean Patent Application No. 10-2008-0078334 filed in the Korean Intellectual Property Office on Aug. 11, 2008, the entire contents of which are incorporated herein by reference.

While the present invention has been described with respect to the specific embodiments, it will be apparent to those skilled in the art that various changes and modifications may be made without departing from the spirit and scope of the invention as defined in the following claims.

The invention claimed is:

1. A preparation method of organic-transition metal hydride comprising the following steps:
   a) preparing a complex reducing agent composition by reacting alkali metal, alkali earth metal or a mixture thereof with (C10-C20) aromatic compound in aprotic polar solvent; and
   b) preparing organic-transition metal hydride by reacting the prepared complex reducing agent composition and organic-transition metal halide;
   wherein the organic-transition metal hydride is selected from those compounds represented by formula 3 and the organic transition metal halide is selected from those compounds represented by formula 4

$$B^2\text{-}(M^2H_a)_b \qquad \text{Formula 3}$$

$$B^2\text{-}(M^2X_a)_b \qquad \text{Formula 4}$$

(In formula 3 and formula 4, B$^2$ should be selected from the group consisting of cyclopentadiene, cyclopentadiene derivatives, and fused ring compounds containing cyclopentadiene or cyclopentadiene derivatives, B$^2$ can be replaced with one or more substituents selected from the group consisting of —NO$_2$, —NO, —NH$_2$, —R$^1$, —OR$^2$, —(CO)R$^3$, —SO$_2$NH$_2$, SO$_2$X$^1$, —SO$_2$Na, —(CH$_2$)$_k$SH and —CN, and in that case, R$^1$-R$^3$ of the substituent can be selected from the group consisting of straight or branched (C1-C30) alkyls and (C6-C20) aryls, respectively;

X$^1$ is a halogen element, and k is an integer of 0-10, M$^2$ is one or more transition metal elements having the valence of at least 2, a is an integer that a valence of M$^2$−1, and b is an integer of 1-10).

2. The preparation method of organic-transition metal hydride according to claim 1, wherein the fused ring compound containing cyclopentadiene derivatives or cyclopentadiene in the B$^2$ is selected from the group consisting of cyclopentadienyl, methylcyclopentadienyl, dimethylcyclopentadienyl, tetramethylcyclopentadienyl, pentamethylcyclopentadienyl, butylcyclopentadienyl, sec-butylcyclopentadienyl, tert-butylmethylcyclopentadienyl, trimethylsilylcyclopentadienyl, indenyl, methylindenyl, dimethylindenyl, ethylindenyl, isopropylindenyl, fluorenyl, methylfluorenyl, dimethylfluorenyl, ethylfluorenyl and isopropylfluorenyl.

3. The preparation method of organic-transition metal hydride according to claim 1, wherein the $M^2$ is one or more elements selected from the group consisting of Ti, V and Sc, the a is an integer of 2-4, and the b is an integer of 2-6.

4. The preparation method of organic-transition metal hydride according to claim 1, wherein the aprotic polar solvent is one or more compounds selected from the group consisting of tetrahydrofuran (THF), 1,2-dimethoxyethane (DME), dioxane (DXN), diethylene glycol dimethyl ether (Diglyme), dimethyl formamide (DMF), dimethylsulfoxide (DMSO), dimethylacetamide (DMA), hexamethyl phosphoramide (HMPA) and their derivatives.

5. The preparation method of organic-transition metal hydride according to claim 2, wherein the aprotic polar solvent is one or more compounds selected from the group consisting of tetrahydrofuran (THF), 1,2-dimethoxyethane (DME), dioxane (DXN), diethylene glycol dimethyl ether (Diglyme), dimethyl formamide (DMF), dimethylsulfoxide (DMSO), dimethylacetamide (DMA), hexamethyl phosphoramide (HMPA) and their derivatives.

6. The preparation method of organic-transition metal hydride according to claim 3, wherein the aprotic polar solvent is one or more compounds selected from the group consisting of tetrahydrofuran (THF), 1,2-dimethoxyethane (DME), dioxane (DXN), diethylene glycol dimethyl ether (Diglyme), dimethyl formamide (DMF), dimethylsulfoxide (DMSO), dimethylacetamide (DMA), hexamethyl phosphoramide (HMPA) and their derivatives.

* * * * *